US011786129B2

(12) United States Patent
Karanam et al.

(10) Patent No.: US 11,786,129 B2
(45) Date of Patent: Oct. 17, 2023

(54) SYSTEMS AND METHODS FOR HUMAN MESH RECOVERY

(71) Applicant: SHANGHAI UNITED IMAGING INTELLIGENCE CO., LTD., Shanghai (CN)

(72) Inventors: Srikrishna Karanam, Bangalore (IN); Ziyan Wu, Lexington, MA (US); Georgios Georgakis, Philadelphia, PA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 0 days.

(21) Appl. No.: 17/666,319

(22) Filed: Feb. 7, 2022

(65) Prior Publication Data
US 2022/0165396 A1    May 26, 2022

Related U.S. Application Data

(63) Continuation of application No. 16/863,382, filed on Apr. 30, 2020, now Pat. No. 11,257,586.
(Continued)

(51) Int. Cl.
*G06K 9/00* (2022.01)
*A61B 5/00* (2006.01)
(Continued)

(52) U.S. Cl.
CPC .......... *A61B 5/0077* (2013.01); *A61B 5/0035* (2013.01); *A61B 5/70* (2013.01);
(Continued)

(58) Field of Classification Search
None
See application file for complete search history.

(56) References Cited

U.S. PATENT DOCUMENTS 11,062,476 B1 * 7/2021 Bigontina ............... G06T 13/80
11,257,586 B2 * 2/2022 Karanam ............... G06V 40/20
(Continued)

OTHER PUBLICATIONS

Guler et al., "DensePose: Dense Human Pose Estimation in the Wild", 2018, CVF, pp. 7297-7306.
(Continued)

*Primary Examiner* — Soo Jin Park
(74) *Attorney, Agent, or Firm* — Zhong Law LLC

(57) ABSTRACT

Human mesh model recovery may utilize prior knowledge of the hierarchical structural correlation between different parts of a human body. Such structural correlation may be between a root kinematic chain of the human body and a head or limb kinematic chain of the human body. Shape and/or pose parameters relating to the human mesh model may be determined by first determining the parameters associated with the root kinematic chain and then using those parameters to predict the parameters associated with the head or limb kinematic chain. Such a task can be accomplished using a system comprising one or more processors and one or more storage devices storing instructions that, when executed by the one or more processors, cause the one or more processors to implement one or more neural networks trained to perform functions related to the task.

18 Claims, 7 Drawing Sheets

Related U.S. Application Data

(60) Provisional application No. 62/941,203, filed on Nov. 27, 2019.

(51) Int. Cl.

| | |
|---|---|
| *G16H 30/40* | (2018.01) |
| *G06T 7/00* | (2017.01) |
| *G06T 7/90* | (2017.01) |
| *G06T 17/00* | (2006.01) |
| *G06T 7/50* | (2017.01) |
| *G06T 7/70* | (2017.01) |
| *G06T 17/20* | (2006.01) |
| *G16H 10/60* | (2018.01) |
| *G16H 30/20* | (2018.01) |
| *G06V 20/64* | (2022.01) |
| *G06V 40/10* | (2022.01) |
| *G06V 40/20* | (2022.01) |
| *G06V 20/62* | (2022.01) |
| *G06F 18/21* | (2023.01) |
| *G06F 18/214* | (2023.01) |
| *G06V 10/764* | (2022.01) |
| *G06V 10/774* | (2022.01) |
| *G06V 10/778* | (2022.01) |
| *G06V 10/82* | (2022.01) |
| *G06V 10/42* | (2022.01) |
| *G06V 10/40* | (2022.01) |

(52) U.S. Cl.
CPC ............ *G06F 18/21* (2023.01); *G06F 18/214* (2023.01); *G06F 18/2193* (2023.01); *G06T 7/0012* (2013.01); *G06T 7/50* (2017.01); *G06T 7/70* (2017.01); *G06T 7/90* (2017.01); *G06T 17/00* (2013.01); *G06T 17/20* (2013.01); *G06V 10/40* (2022.01); *G06V 10/42* (2022.01); *G06V 10/764* (2022.01); *G06V 10/774* (2022.01); *G06V 10/7796* (2022.01); *G06V 10/82* (2022.01); *G06V 20/62* (2022.01); *G06V 20/64* (2022.01); *G06V 40/10* (2022.01); *G06V 40/20* (2022.01); *G16H 10/60* (2018.01); *G16H 30/20* (2018.01); *G16H 30/40* (2018.01); *G06T 2200/08* (2013.01); *G06T 2207/10024* (2013.01); *G06T 2207/20081* (2013.01); *G06T 2207/20084* (2013.01); *G06T 2207/30004* (2013.01); *G06T 2207/30196* (2013.01); *G06V 2201/033* (2022.01)

(56) References Cited

U.S. PATENT DOCUMENTS

| | | | |
|---|---|---|---|
| 2012/0056800 A1 | 3/2012 | Williams et al. | |
| 2020/0327418 A1* | 10/2020 | Lyons | G06V 40/11 |
| 2020/0342270 A1 | 10/2020 | Biswas et al. | |
| 2021/0019507 A1* | 1/2021 | Brookshire | G06V 40/25 |
| 2021/0027484 A1 | 1/2021 | Chen | |
| 2021/0097718 A1 | 4/2021 | Fisch | |
| 2021/0150806 A1 | 5/2021 | Guler et al. | |

OTHER PUBLICATIONS

Arnab et al., "Exploiting Temporal Context for 3D Human Pose Estimation in the Wild", 2019, CVF, pp. 3395-3404.
Bahdanau et al., "Neural Machine Translation by Jointly Learning to Align and Translate", ICLR, 2015, arXiv:1409.0473v7 [cs.CL], pp. 1-15.
Belghit et al., "Vision-Based Pose Estimation for Augmented Reality: A Comparison Study", IEEE, 2018, pp. 1-8.
Bogo et al., "Keep It SMPL: Automatic Estimation of 3D Human Pose and Shape from a Single Image", Computer Vision and Pattern Recognition, 2016, pp. 561-578.
Cao et al., "Realtime Multi-Person 2D Pose Estimation Using Part Affinity Fields", CVF, 2017, pp. 7291-7299.
Chen et al., 3D Human Pose Estimation + 2D Pose Estimation + Matching, CVF, 2016, pp. 7035-7043.
Chen et al., "Synthesizing Training Images for Boosting Human 3D Pose Estimation", arXiv:1604.02703v6 [cs.CV] Jan. 5, 2017, pp. 4321-4330.
Chen et al., "Weakly-Supervised Discovery of Geometry-Aware Representation for 3D Human Pose Estimation", CVF, 2019, pp. 10895-10904.
Liu et al., "PKU-MMD: A Large Scale Benchmark for Continuous Multi-Modal Human Action Understanding", arXiv:1703.07475v2 [cs.CV] Mar. 28, 2017, pp. 1-10.
Deprelle et al., "Learning Elementary Structures for 3D Shape Generation and Matching", arXiv:1908.04725v2 [cs.CV] Aug. 14, 2019, pp. 1-11.
Groueix et al., "3D-Coded: 3D Correspondences by Deep Deformation", CVF, 2018, pp. 1-17.
Gupta et al., "3D Pose from Motion for Cross-View Action Recognition via Non-linear Circulant Temporal Encoding", CVF, 2014, pp. 1-8.
He et al., "Deep Residual Learning for Image Recognition", CVF, 2015, pp. 770-778.
He et al., "Identity Mappings in Deep Residual Networks", arXiv:1603.05027v3 [cs.CV] Jul. 25, 2016. pp. 1-15.
Jahangiri et al., "Generating Multiple Diverse Hypotheses for Human 3D Pose Consistent with 2D Joint Detections", IEEE, 2017, pp. 805-814.
Hao Jiang, "3D Human Pose Reconstruction Using Millions of Exemplars", International Conference on Pattern Recognition, 2010, pp. 1674-1677.
Johnson et al., "Clustered Pose and Nonlinear Appearance Models for Human Pose Estimation", BMVC, 2010, pp. 1-11.
Kadkhodamohammadi et al., "A Multi-View RGB-D Approach for Human Pose Estimation in Operating Rooms," IEEE, 2017, pp. 363-372.
Kanazawa et al., "End-To-End Recovery of Human Shape and Pose", CVF, 2017, pp. 7122-7131.
Kanazawa et al., "Learning 3D Human Dynamics from Video", CVF, 2019, pp. 5614-5623.
Kocabas et al., "Self-Supervised Learning of 3D Human Pose Using Multi-View Geometry", CVF, 2019, pp. 1077-1086.
Kohli et al., "Key Developments in Human Pose Estimation for Kinect", Advances in Computer Vision and Pattern Recognition, 2013, pp. 63-70.
Kolotouros et al., "Convolutional Mesh Regression for Single-Image Human Shape Reconstruction", CVF, 2019, pp. 4501-4510.
Lassner et al., "Unite the People: Closing the Loop Between 3D and 2D Human Representations", CVF, 2017, pp. 6050-6059.
Levine et al., "End-To-End Training of Deep Visuomotor Policies", Journal of Machine Learning Research 17, 2016, pp. 1-40.
Liang et al., "Shape-Aware Human Pose and Shape Reconstruction Using Multi-View Images", CVF, 2019, pp. 4352-4362.
Lin et al., "Microsoft COCO: Common Objects in Context", Springer International Publishing Switzerland, 2014, pp. 740-755.
Looper et al., "MoSh: Motion and Shape Capture from Sparse Markers", ACM Transactions on Graphics, vol. 33, No. 6, 2014, pp. 1-13.
Looper et al., "SMPL: A Skinned Multi-Person Linear Model", ACM Transactions on Graphics, 2015, pp. 1-16.
Martinez et al., "A Simple Yet Effective Baseline for 3D Human Pose Estimation", CVF, 2017, pp. 2640-2649.
Martinez-Gonzalez et al., "Reall-time Convolutional Networks for Depth-Based Human Pose Estimation", IDIAP Research Institute, 2018, pp. 1-7.
Mehta et al., "VNect: Real-time 3D Human Pose Estimation with a Single RGB Camera", ACM Transactions on Graphics, vol. 36, No. 4, 2017, pp. 1-14.

(56) References Cited

OTHER PUBLICATIONS

Moeslund et al., "A Survey of Computer Vision-Based Human Motion Capture" Computer Vision and Image Understanding 81, 2001, pp. 231-268.
Moeslund et al., "A Survey of Advances in Vision-Based Human Motion Capture", Elsevier, 2006, pp. 90-126.
Newell et al., "Stacked Hourglass Networks for Human Pose Estimation", arXiv:1603.06937v2 [cs.CV] Jul. 26, 2016, pp. 1-17.
Obdrzalek et al., "Accuracy and Robustness of Kinect Pose Estimation in the Context of Coaching of Elderly Population", IEEE, 2012, pp. 1188-1193.
Paszke et al., "Automatic Differentiation in PyTorch" 31st Conference on Neural Information Processing Systems, 2017, pp. 1-4.
Pavlakos et al., "Ordinal Depth Supervision for 3D Human Pose Estimation", CVF, 2018, pp. 7307-7316.
Pavlakos et al., "Coarse-To-Fine Volumetric Prediction for Single-Image 3D Human Pose", CVF, 2017, pp. 7025-7034.
Peng et al., "Jointly Optimize Data Augmentation and Network Training Adversarial Data Augmentation in Human Pose Estimation", CVF, 2018, pp. 2226-2234.
Rhodin et al., "Neural Scene Decomposition for Multi-Person Motion Capture", CVF, 2019, pp. 7703-7713.
Rhodin et al., "Unsupervised Geometry-Aware Representation for 3D Human Pose Estimation", CVF 2018, pp. 1-18.
Rogez et al., "MoCap-Guided Data Augmentation for 3D Pose Estimation in the Wild", Computer Vision and Pattern Recognition, 2016, pp. 1-9.
Sarafianos et al., "3D Human Pose Estimation: A Review of the Literature and Analysis of Covariates" Elsevier, Computer Vision and Image Understanding, 2016, pp. 1-20.
Sharma et al., "Monocular 3D Human Pose Estimation by Generation and Ordinal Ranking", CVF, 2019, pp. 2325-2334.
Sun et al., "Integral Human Pose Regression" CVF, 2018, pp. 1-17.
Sung et al., "Unstructured Human Activity Detection from RGBD Images", IEEE, 2012, pp. 1-8.
Varol et al., "Learning from Synthetic Humans", CVF, 2017, pp. 109-117.
Wandt et al., "RepNet: Weakly Supervised Training of an Adversarial Reprojection Network for 3D Human Pose Estimation", CVF, 2019, pp. 7782-7791.
Wei et al., "Convolutional Pose Machines" CVF, 2016, pp. 4724-4732.
Zhou et al., "Towards 3D Human Pose Estimation in theWild: aWeakly-supervised Approach", CVF, 2017, pp. 398-407.
Zimmermann et al., "3D Human Pose Estimation in RGBD Images for Robotic Task Learning",arXiv:1803.02622v2 [cs.CV] Mar. 13, 2018, pp. 1-7.

* cited by examiner

SYSTEMS AND METHODS FOR HUMAN MESH RECOVERY

This application is a continuation of U.S. patent application Ser. No. 16/863,382, filed Apr. 30, 2020, which claims the benefit of Provisional U.S. Patent Application No. 62/941,203, filed Nov. 27, 2019, the disclosure of which is incorporated herein by reference in its entirety.

BACKGROUND

Human mesh models that realistically reflect a patient's shape and pose can be used in a variety of medical applications including patient positioning, surgical navigation, unified medical record analysis, etc. For example, with radiation therapy and medical imaging, success often hinges upon the ability to place and maintain a patient in a desirable position so that the treatment or scan can be performed in a precise and accurate manner. Having real time knowledge about the patient's physical characteristics such as the patient's body shape and pose in these situations may bring many benefits including, for example, faster and more accurate positioning of the patient in accordance with a scan or treatment protocol, more consistent results, etc. In other example situations such as during a surgical procedure, information about a patient's physiques may offer insight and guidance for both treatment planning and execution. The information may be utilized, for instance, to locate and navigate around a treatment site of the patient. When visually presented in real time, the information may also provide means for monitoring the state of the patient during the procedure.

Conventional human mesh recovery (HMR) systems and methods work on the assumption that substantial portions of a human body are visible (e.g., unoccluded) for inferring the shape and pose of the human body. In many medical environments, however, a patient's body is often blocked, at least partially, by medical equipment and/or closing items. Therefore, it is highly desirable for HMR systems and methods to have the ability to accurately recover a mesh of a patient's body despite having one or more portions of the patient's body blocked by other objects. Further, in estimating the parameters for constructing a human mesh model, conventional HMR systems and methods often take a black-box approach without considering the structural correlation between different parts of the human body, which could provide valuable insight into the shape and/or pose of the human body. So, it is also desirable for HMR systems and methods to utilize knowledge about the structure of the human body to improve the accuracy of HMR.

SUMMARY

Described herein are systems, methods and instrumentalities for recovering a human model based on an input image of a person. The systems, methods and/or instrumentalities may utilize one or more processors and one or more storage devices storing instructions that, when executed by the one or more processors, cause the one or more processors to implement one or more neural networks. The one or more neural networks may be trained on a plurality of training images to identify features presented in the training images and infer joint angles associated with a root kinematic chain based on the identified features. The one or more neural networks may be further trained to infer joint angles associated with a head or limb kinematic chain based on the identified features and the joint angles associated with the root kinematic chain. The root kinematic chain may comprise at least a chest area or a pelvis area of the human body, and the head or limb kinematic chain comprises at least a head area or a limb area of the human body.

Utilizing at least the one or more neural networks described above, the one or more processors may identify a set of features in the input image of the person and determine a first plurality of joint angles associated with the root kinematic chain based on the set of features identified in the input image of the person. The one or more processors may further determine a second plurality of joint angles associated with the head or limb kinematic chain based on the set of features identified in the input image of the person and the first plurality of joint angles associated with the root kinematic chain. The first and second pluralities of joint angles may then be used, together with the set of features identified in the input image, to estimate a human model for the person.

In addition to the joint angles, the one or more processors described herein may be further configured to determine at least one shape parameter of the person and estimate the human model for the person based further on the at least one shape parameter of the person. The human model comprises a skinned multi-person linear (SMPL) model and the one or more processors may output a representation of the human model to a receiving device associated with a medical imaging modality.

The head or limb kinematic chain described herein may comprise one or more of the following chains: a first chain comprising the left shoulder, left elbow, left wrist and left hand of the human body; a second chain comprising the right shoulder, right elbow, right wrist and right hand of the human body; a third chain comprising the left hip, left knee, left ankle and left foot of the human body; a fourth chain comprising the right hip, right knee, right ankle and right foot of the human body; or a fifth chain comprising the head and neck of the human body. For each of these kinematic chains, the neural networks may be trained to predict a target joint angle (e.g., which may be associated with an end effector of the kinematic chain) based on one or more other joints associated with the kinematic chain. The training of the neural networks may comprise randomly skipping at least one of the one or more other joints and making the neural networks to still predict the target joint angle based on the remaining joints. The training of the neural networks may also comprise adjusting filtering parameters of the one or more neural networks based on an objective function configured to indicate a difference between an output of the neural networks and a ground truth associated with the output. Such an objective function may comprise, for example, a mean squared error (MSE) function.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
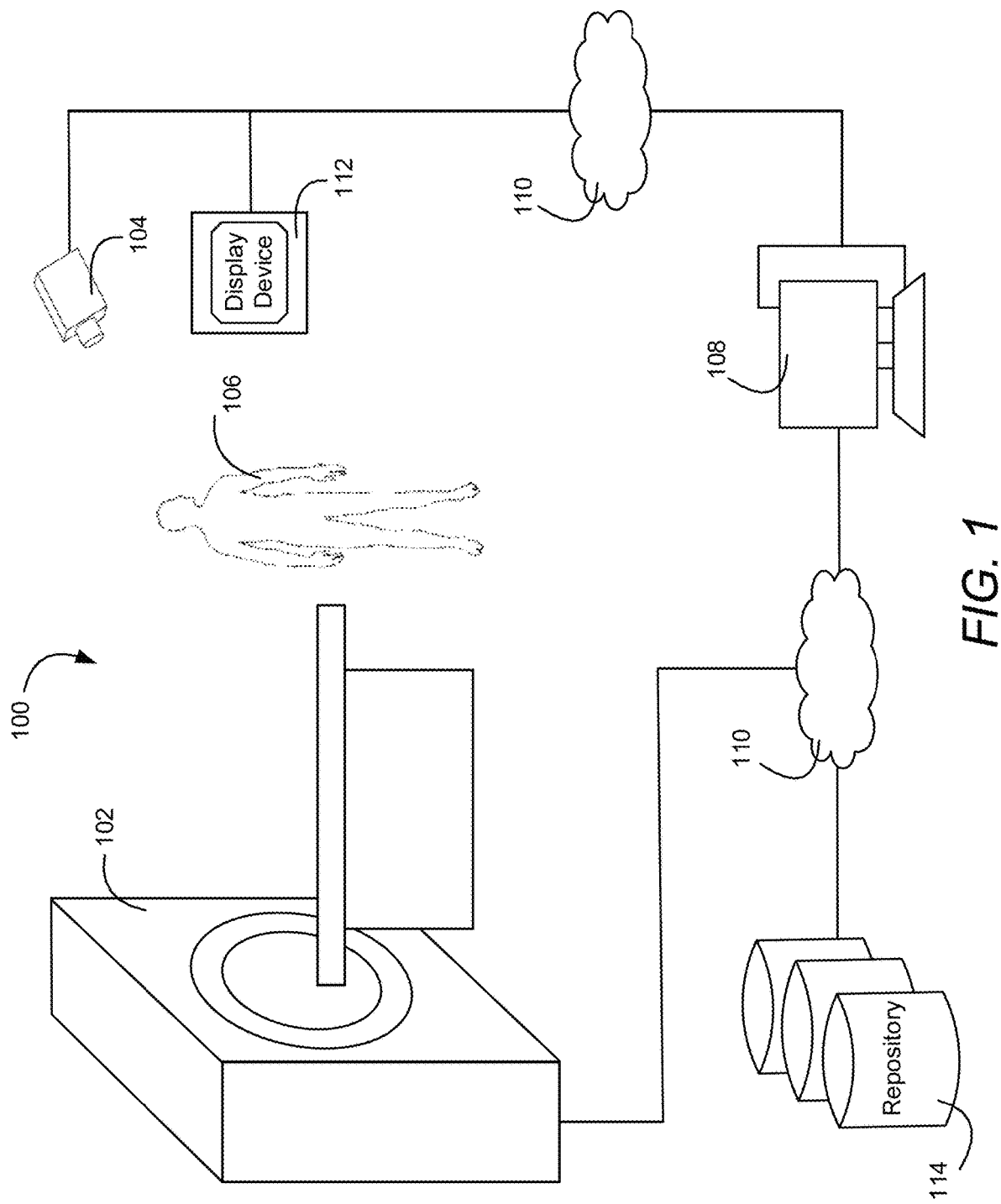
FIG. 1 is a simplified block diagram illustrating an example system in which one or more of the examples described herein may be implemented.

FIG. 1 is a diagram illustrating an example system 100 that may utilize the systems, methods and instrumentalities disclosed herein to recover a human mesh model. As shown in the figure, the system 100 may be configured to provide a medical scan or imaging procedure conducted using a medical scanner 102 (e.g., a computer tomography (CT) scanner, a magnetic resonance imaging (MRI) machine, a positron emission tomography (PET) scanner, an X-ray machine, etc.), even though the system 100 may also be adapted to provide other types of healthcare services including, for example, radiation therapy, surgery, etc.

The system 100 may include at least one sensing device 104 (e.g., an image capturing device) configured to capture images of a patient 106, for example, in front of the medical scanner 102, lying on a scan or treatment bed, etc. The sensing device 104 may comprise one or more sensors including one or more cameras (e.g., digital color cameras, 3D cameras, etc.), one or more red, green and blue (RGB) sensors, one or more depth sensors, one or more RGB plus depth (RGB-D) sensors, one or more thermal sensors such as infrared (FIR) or near-infrared (NIR) sensors, and/or the like. Depending on the type of sensors used, the images captured by the sensing device 104 may include, for example, one or more photos of the patient taken by a camera, one or more 2D RGB images generated by an RBG sensor, etc. The sensing device 104 may be installed or placed in various locations of the system 100 and the locations may affect the field of view (FOV) of the sensing device 104. For example, depending on the specific installation location of the sensing device and/or the position of the patient 106, the sensing device 104 may be able to capture only a partial picture of the patient (e.g., certain parts of the patient's body may be blocked from the FOV of the sensing device 104).

The sensing device 104 may include one or more processors configured to process the images of the patient captured by the sensors described herein. Additionally or alternatively, the system 100 may include a processing device 108 communicatively coupled to the sensing device 104 and configured to process the images of the patient captured by the sensing device 104. The processing device 108 may be coupled to the sensing device 104 (e.g., to the sensors comprised in the sensing device 104), for example, via a communication network 110, which may be a wired or wireless communication network. In response to receiving the images of the patient, the sensing device 104 and/or the processing device 108 may analyze the images (e.g., at a pixel level) and generate a 2D or 3D human mesh model for the patient. The human mesh model may include, for example, a parametric model such as a skinned multi-person linear (SMPL) model that indicates the shape, pose, and/or other anatomical characteristics of the patient.

The human mesh model generated by the sensing device 104 and/or the processing device 108 may be used to facilitate a plurality of downstream medical applications and services including, for example, patient positioning, medical protocol design, unified or correlated diagnoses and treatments, patient monitoring, surgical navigation, etc. For example, the processing device 108 may determine, based on the human mesh model, whether the position and/or pose of the patient meets the requirements of a predetermined protocol and provide real-time confirmation or adjustment instructions (e.g., while the patient is standing in front of the medical scanner or lying on a scan bed), e.g., via the display device 112, to help the patient get into the desirable position and/or pose. The processing device 108 may also control (e.g., adjust) one or more operating parameters of the medical scanner 102 such as the height of the scan bed based on the body shape of the patient indicated by the human mesh model. As another example, the sensing device 104 and/or the processing device 108 may be coupled with a medical record repository 114 configured to store patient medical records including scan images of the patient obtained through other imaging modalities (e.g., CT, MR, X-ray, SPECT, PET, etc.). The processing device 112 may analyze the medical records stored in the repository 114 using the human mesh model as reference so as to obtain a comprehensive understanding of the patient's medical conditions. For instance, the processing device 112 may align scan image of the patient from the repository 114 with the human mesh model to allow the scan images to be presented and analyzed with reference to the anatomical characteristics (e.g., body shape and/or pose) of the patient as indicated by the human mesh model.

Figure 2:
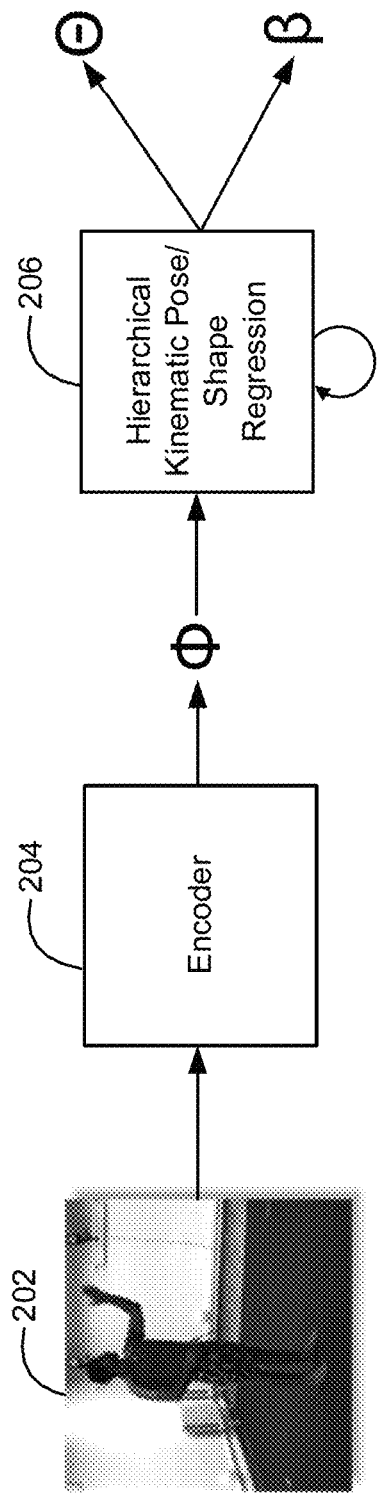
FIG. 2 is a simplified block diagram illustrating how a human mesh model may be recovered based on a 2D image of a person.

FIG. 2 shows a simplified block diagram illustrating how a human mesh model may be recovered based on a 2D image of a person. As shown, given an input image 202 of the person, a plurality of features, Φ, may be extracted from the image, for example, using an encoder module 204. The extracted features may be provided to a hierarchical kinematic pose/shape regression module 206, which may be configured to infer parameters from the extracted features for recovering the human mesh model. The inferred parameters may include, for example, one or more pose parameters, Θ, and one or more shape parameters, β, that may respectively indicate the pose and shape of the person's body.

The encoder module 204 and/or the hierarchical kinematic pose/shape regression module 206 may comprise one or more processors and one or more storage devices. The storage devices may be configured to store instructions that, when executed by the one or more processors, cause the one or more processors to implement one or more neural networks such as one or more convolutional neural networks (CNNs) and/or one or more deep neural networks (DNNs). The one or more processors may include a central processing unit (CPU), a graphics processing unit (GPU), a microcontroller, a reduced instruction set computer (RISC) processor, an application specific integrated circuit (ASIC), an application-specific instruction-set processor (ASIP), a physics processing unit (PPU), a digital signal processor (DSP), a field programmable gate array (FPGA), or a combination thereof. The one or more storage devices may include volatile or non-volatile memory such as semiconductor memory (e.g., electrically programmable read-only memory (EPROM), electrically erasable programmable read-only memory (EEPROM), etc.), flash memory, a mass storage device (e.g., a magnetic disk such as an internal hard disk, a removable disk, a magneto-optical disk, a CD-ROM or DVD-ROM disk, etc.).

Each of the one or more neural networks may comprise multiple layers such as an input layer, one or more convolutional layers, one or more non-linear activation layers, one or more pooling layers, one or more fully connected layers, and/or an output layer. Each of the layers may correspond to a plurality of filters (e.g., kernels) and each filter may be designed to detect (e.g., learn) a set of keypoints that collectively represent a respective feature or pattern. The filters may be associated with respective weights that, when applied to an input, produce an output indicating whether certain visual features or patterns have been detected. The weights associated with the filters may be learned by the neural networks through a training process that comprises inputting a large number of images from one or more training datasets to the neural networks, calculating differences or losses resulting from the weights currently assigned to the filters (e.g., based on an objective function such as mean squared error or L1 norm, a margin based loss function, etc.), and updating the weights assigned to the filters so as to minimize the differences or losses (e.g., based on stochastic gradient descent). Once trained (e.g., having learned to recognize features and/or patterns in the training images), the neural networks may take an image at the input layer, extract and/or classify visual features or patterns from the image, and provide an indication at the output layer for an identified feature or feature class. The identified feature may be indicated, for example, with a feature descriptor or feature vector.

The one or more neural networks may also be trained to infer, e.g., based on features extracted from an input image, pose and shape parameters for recovering a 3D human model. For example, the one or more neural networks may be trained to determine, based datasets that cover a wide range of human subjects, human activities, background noises, shape and/or pose variations, camera motions, etc., the joint angles of a plurality of joints of a person as depicted in an input image. The plurality of joints may include, for example, 23 joints comprised in a skeletal rig as well as a root joint, and the pose parameters derived thereof may include 72 parameters (e.g., 3 parameters for each of the 23 joints and 3 parameters for the root joint, with each parameter corresponding to an axis-angle rotation from a root orientation). The neural networks may also learn to determine, based on the training datasets, one or more shape parameters for predicting a blend shape of a person based on an image of the person. For example, the neural networks may learn to determine the shape the parameters by conducting principle component analysis (PCA) and the shape parameters thus determined may include a plurality of coefficients (e.g., the first 10 coefficients) of the PCA space. Once the pose and shape parameters are determined, a plurality of vertices (e.g., 6890 vertices based on 82 shape and pose parameters) may be obtained for constructing a representation (e.g., a 3D mesh) of the human body. Each of the vertices may include respective position, normal, texture, and/or shading information. Using these vertices, a 3D mesh of the person may be created, for example, by connecting multiple vertices with edges to form a polygon (e.g., such as a triangle), connecting multiple polygons to form a surface, using multiple surfaces to determine a 3D shape, and applying texture and/or shading to the surfaces and/or shapes.

The neural networks described herein may be trained to consider structural correlation between different parts of the human body when estimating the pose and/or shape parameters of a human model. Such structural correlation may provide additional insight or information to the neural networks with respect to how the position and/or orientation of one part of the human body may be affected by the position and/or orientation of another part of the human body and the neural networks may utilize such additional information to improve the accuracy of parameter estimation, even in situations where one or more parts of the human body are occluded.

Figure 3:
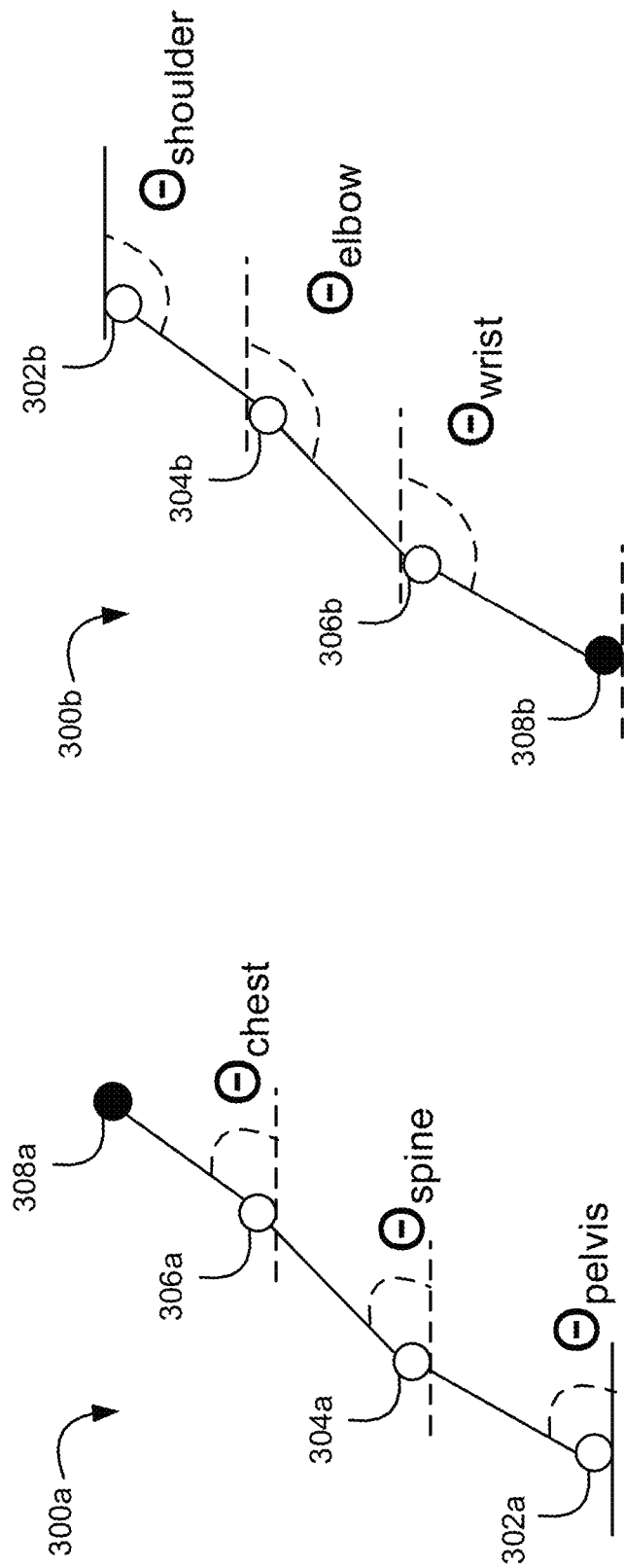
FIG. 3A is an example block diagram illustrating a root kinematic chain of a human body.
FIG. 3B is an example block diagram illustrating a limb kinematic chain of a human body.

FIG. 3A is an example block diagram illustrating a root kinematic chain 300a of a human body and FIG. 3B is an example block diagram illustrating a limb (e.g., right shoulder) kinematic chain 300b of a human body. The root kinematic chain 300a may include a plurality of joints in the core section of the human body such as a joint 302a in the pelvis area, one or more joints 304a in the spine, a joint 306a in the chest area and an end effector 308a (e.g., an end area of the root kinematic chain 300a that may be connected to a next kinematic chain of the human body). Similarly, the limb kinematic chain 300b may include a plurality of joints along the right arm of the human body such as a shoulder joint 302b, an elbow joint 304b, a wrist 306b, and an end effector 308b (e.g., a fingertip of the right hand).

As shown, the locations and/or joint angles of each respective kinematics chain (e.g., $\Theta_{pelvis}$, $\Theta_{spine}$, $\Theta_{chest}$ of the root kinematic chains and $\Theta_{shoulder}$, $\Theta_{elbow}$, $\Theta_{wrist}$ of the limb kinematic chains) may be interrelated and as such, knowledge about the locations and/or joint angles of a subset of the joints in a kinematic chain may be used to estimate the locations and/or joint angles of a second subset of the joints in the kinematic chain. The estimation may be performed in a forward direction and/or a backward direction. In an example forward estimation involving the root kinematic chain 300a, the respective locations and/or joint angles of the pelvis joint 302a, the spine joint 304a and the chest joint 306a may be used to estimate the location and/or joint angle of the end effector 308a. Similarly, in an example forward estimation involving the limb kinematic chain 300b, the respective locations and/or joint angles of the shoulder joint 302b, the spine joint 304b and the chest joint 306b may be used to estimate the location and/or joint angle of the end effector 308b (e.g., a fingertip). In the backward direction, the locations and/or joint angles of a subset of joints at or near an end effector may be used to estimate the location and/or joint angle of a joint at or near the beginning segment of a kinematic chain. For example, with the limb kinematic chain 300b, a backward estimation may comprise estimating the location and/or joint angle of the shoulder joint 302b based on the locations and/or angles of the other joints in the kinematic chain including, e.g., one or more of the end effector 308b, wrist 306b, or elbow joint 304b.

Figure 4:
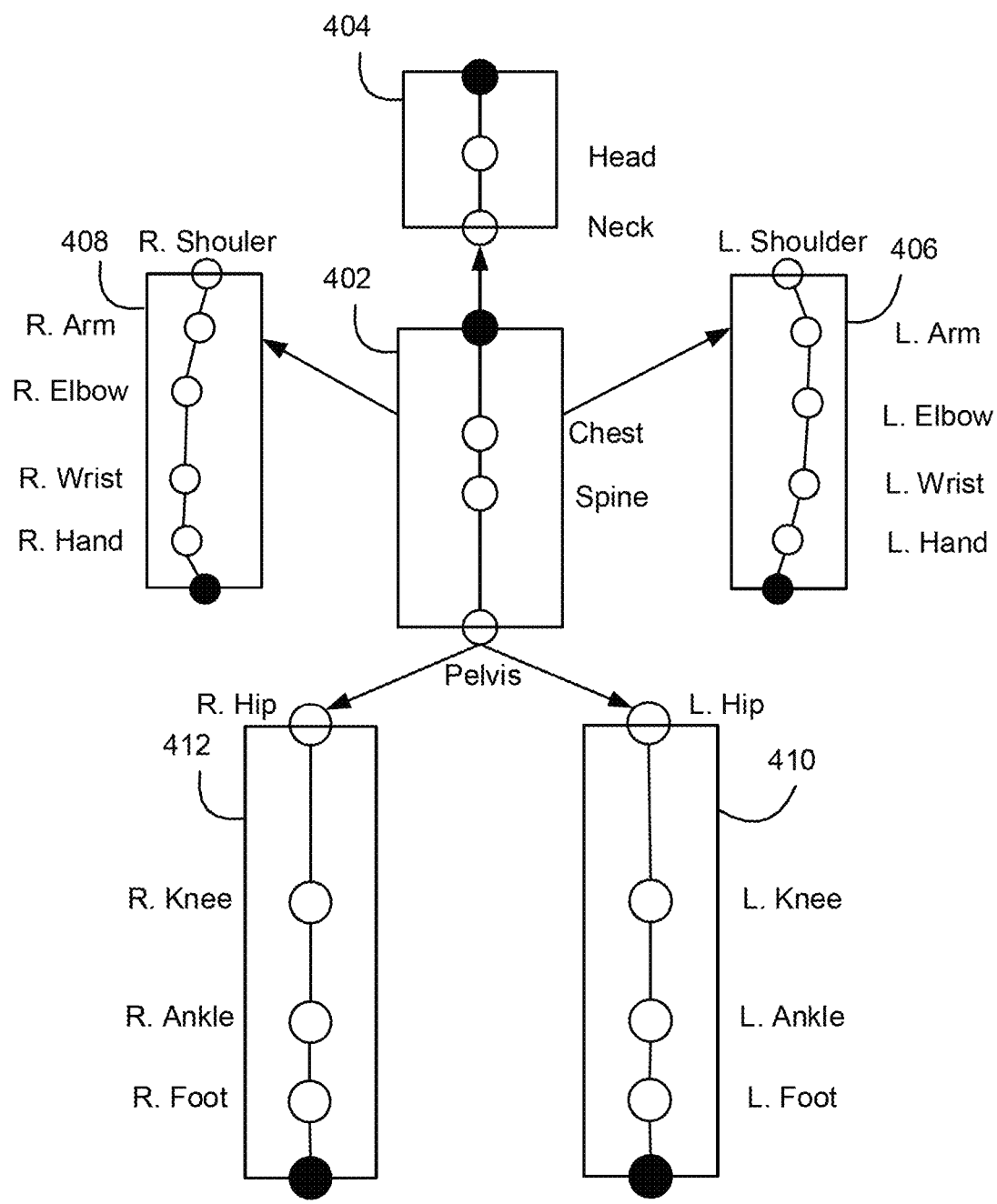
FIG. 4 is an example block diagram illustrating six kinematic chains of a human body.

In addition to the structural correlation between joints within a kinematic chain, the locations and/or joint angles of the joints in the kinematic chain may also be impacted by the locations and/or joint angles of another kinematic chain. FIG. 4 is an example block diagram illustrating six kinematic chains of the human body including a root kinematic chain 402, a head kinematic chain 404, and four limb kinematic chains (e.g., a left arm kinematic chain 406, a right arm kinematic chain 408, a left leg kinematic chain 410, and a right leg kinematic chain 412). As described herein, each of the kinematic chains may comprise a plurality of joints and end effectors such as the pelvis 302a, spine 304a, chest 306a and end effector 308a shown in FIG. 3A and the shoulder 302b, elbow 304b, wrist 306b and end effector 308b shown in FIG. 3B. The kinematic chains may be interrelated to each other. For example, the joint angles of the head kinematic chain 404 and/or the joint angles in the limb kinematic chains 406, 408, 410 and 412 may be dependent on the joint angles of the root kinematic chain 402, e.g., as shown by the arrows in FIG. 4. For instance, when the joint angles of the root kinematic chain 402 are in the state shown in FIG. 4, the human body may be in an upright position and the joint angles of the other kinematic chains may be limited to respective ranges of values as dictated by the upright position of the body. Similarly, when the joint angles of the root kinematic chain 402 move away from the state shown in FIG. 4, e.g., as the human body leans sideways, the joint angles of the other kinematic chains may have different ranges of values as dictated by the new position of the body.

Figure 5:
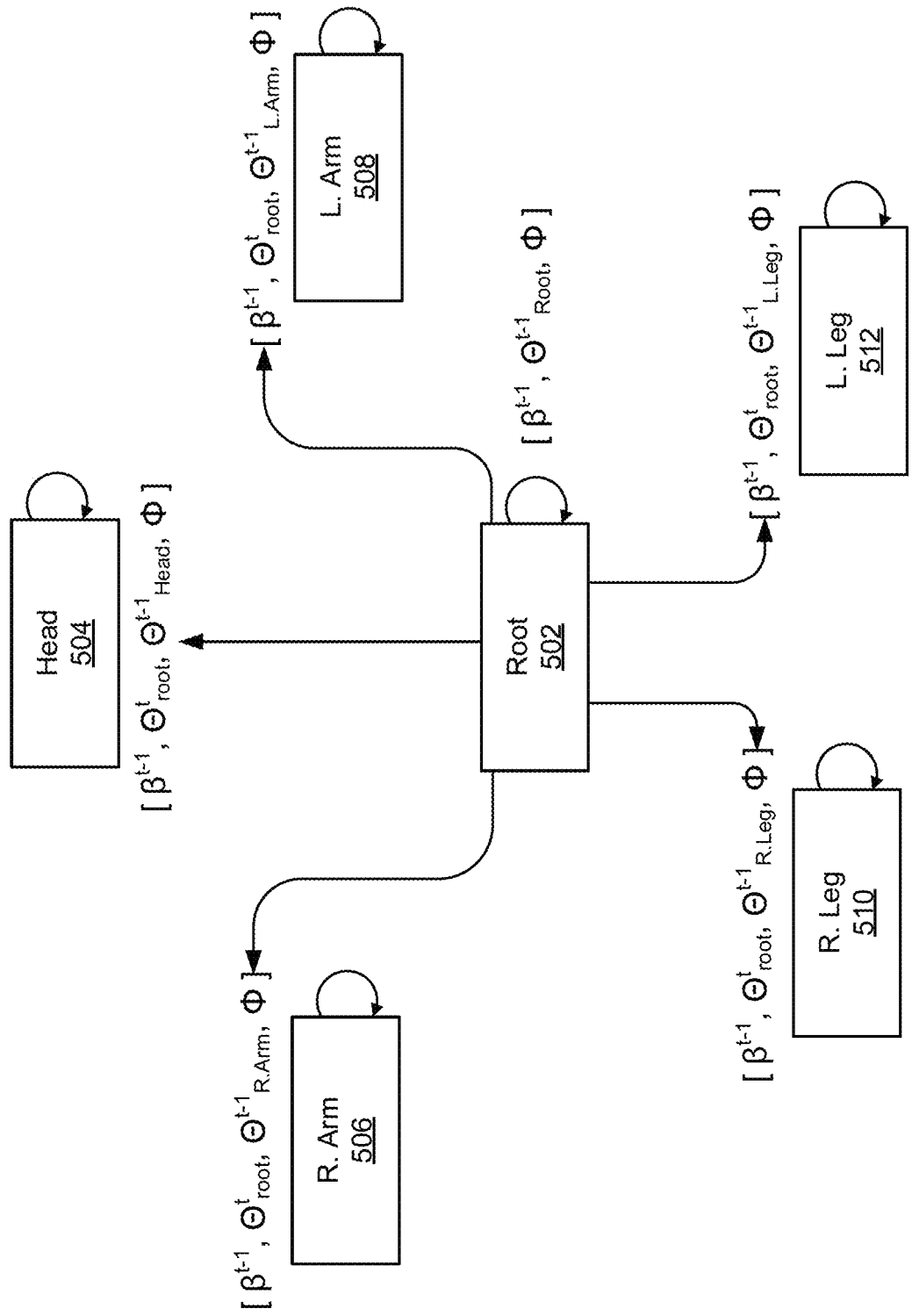
FIG. 5 is a diagram illustrating an example neural network training process.

The one or more neural networks (referred to herein as "the neural network") may be trained to learn the structural correlations between joints and/or kinematic chains. FIG. 5 is a diagram illustrating an example training process for the neural network. As shown, the neural network may be trained to estimate pose parameters $\Theta$ and shape parameters $\beta$ associated with a human mesh model through an iterative process. For instance, during an initial iteration t-1, the neural network may receive an input image and extract a plurality of features $\Phi$ from the input image. The neural network may also initialize the shape parameters to have values $\beta^{t-1}$ and the pose parameters for each of a root chain 502, a head chain 504, a right arm chain 506, a left arm chain 508, a right leg chain 510, and a left right chain 512 to have values $\Theta^{t-1}_{Root}$, $\Theta^{t-1}_{Head}$, $\Theta^{t-1}_{R.Arm}$, $\Theta^{t-1}_{L.arm}$, $\Theta^{t-1}_{R.Leg}$, and $\Theta^{t-1}_{L.Leg}$, respectively. These initial values for the shape and/or pose parameters may be set, for example, based on a normal distribution (e.g., with a certain standard deviation). The neural network may then estimate (e.g., predict) an adjustment $\Delta\Theta$ to the initial values of the pose parameters for the root chain 502, $\Theta^{t-1}_{Root}$, based on the initial values $\Theta^{t-1}_{Root}$, the initial shape parameters $\beta^{t-1}$ and the features $\Phi$ extracted from the input image. The adjustment $\Delta\Theta$ may be applied to the initial values $\Theta^{t-1}_{Root}$ to derive an updated version of the pose parameters for the root chain, $\Theta^{t}_{Root}$ (e.g., based on $\Theta^{t}_{Root}=\Theta^{t-1}_{Root}+\Delta\Theta$). Using the updated pose parameters $\Theta^{t}_{Root}$ for the root chain 502, the neural network may predict respective updated pose parameters for one or more (e.g., for each) of the head or limb chains 504, 506, 508, 510, or 512. For example, the neural network may predict the updated pose parameters for the head kinematic chain 504 based on the updated root chain pose parameters $\Theta^{t}_{Root}$, the initial pose parameters for the head chain $\Theta^{t-1}_{Head}$, the initial shape parameters $\beta^{t-1}$, and the features $\Phi$ extracted from the input image. As another example, the neural network may predict the updated pose parameters for the right arm kinematic chain 506 based on the updated root chain pose parameters $\Theta^{t}_{Root}$, the initial pose parameters for the right arm chain $\Theta^{t-1}_{R.Arm}$, the initial shape parameters $\beta^{t-1}$, and the features $\Phi$ extracted from the input image. The neural network may also update the pose parameters for the other kinematic chains in similar manners.

Once the pose parameters $\Theta$ (e.g., for the respective root chain 502 and the head/limb chains 504-512) have been updated, the neural network may proceed to predict an updated version of the shape parameters, $\beta^t$, based on the initial shape parameters $\beta^{t-1}$, the updated pose parameters $\Theta^t$, and the features $\Phi$ extracted from the input image. The neural network may then use the updated pose parameters $\Theta^t$ (e.g., for the respective root chain 502 and the head/limb chains 504-512), the updated shape parameters $\beta^t$, and the features $\Phi$ as inputs to the next iteration of training and repeat the estimation operations described above until one or more training termination criteria are satisfied (e.g., after completing a pre-determined number of training iterations, upon determining that the change in an objective function falls below a predetermined threshold, etc.). The neural network may optimize its parameters utilizing an objective function that is based on one or more of a mean squared error, L1 norm, etc.

The neural network may also be trained to perform forward and backward estimation within each of the kinematic chains 502, 504, 506, 508, 510, or 512 through an iterative process. For instance, in the forward direction, the neural network may learn to predict the location and/or joint angle of an end effector in the kinematic chain based on the other joint locations and/or joint angles in the kinematic chain. Using the right arm kinematic chain 506 as an example, the neural network may receive, as inputs, an image (e.g., features $\Phi$ extracted from the image) of a person, information regarding the locations and/or joint angles of other joints (e.g., including one or more joints of the right arm kinematic chain 506 and/or joints of the root kinematic chain 502), and/or information regarding the shape of the person. Based on these inputs, the neural network may estimate a location and/or joint angle of an end effector (e.g., a fingertip) of the right arm kinematic chain. The neural network may compare the estimated location and/or joint angle of the end effector with a ground truth for the location and/or joint angle, and determine an update to the relevant filtering weights or parameters (e.g., relating to the right arm kinematic chain) based on an objective function (e.g., a loss function). The objective function may be implemented, for example, based on one or more of a mean squared error, L1 norm, etc., and the neural network may update the filtering weights or parameters using a back-propagation procedure (e.g., by determining a gradient of the objective function with respect to the current filtering weights or parameters). The neural network may then repeat the foregoing process using the updated parameters until one or more training termination criteria are satisfied (e.g., after completing a pre-determined number of training iterations, if the change in the value of the objective function between training iterations falls below a predetermined threshold, etc.).

In the backward direction, the neural network may be trained in a similar manner to predict the location and/or joint angle of a joint at or near the beginning segment of a kinematic chain based on an end effector of the kinematic chain and/or other joints comprised in the chain. For instance, the neural network may be given information regarding the locations and/or angles of a fingertip and other joints (e.g., such as right wrist, right hand, and/or right elbow comprised in the kinematic chain and/or the joints in the root kinematic chain 502), and the neural network may use the given joint information together with the features $\Phi$ and the shape of the person to learn the parameters for predicting the location and/or joint angle of the right shoulder. Such training in the backward direction may help improve the neural network's ability to estimate a joint location and/or joint angle in the forward direction, e.g., when a part of the human body is occluded or obstructed. Greater detail about this feature will be provided in an example below.

Figure 6:
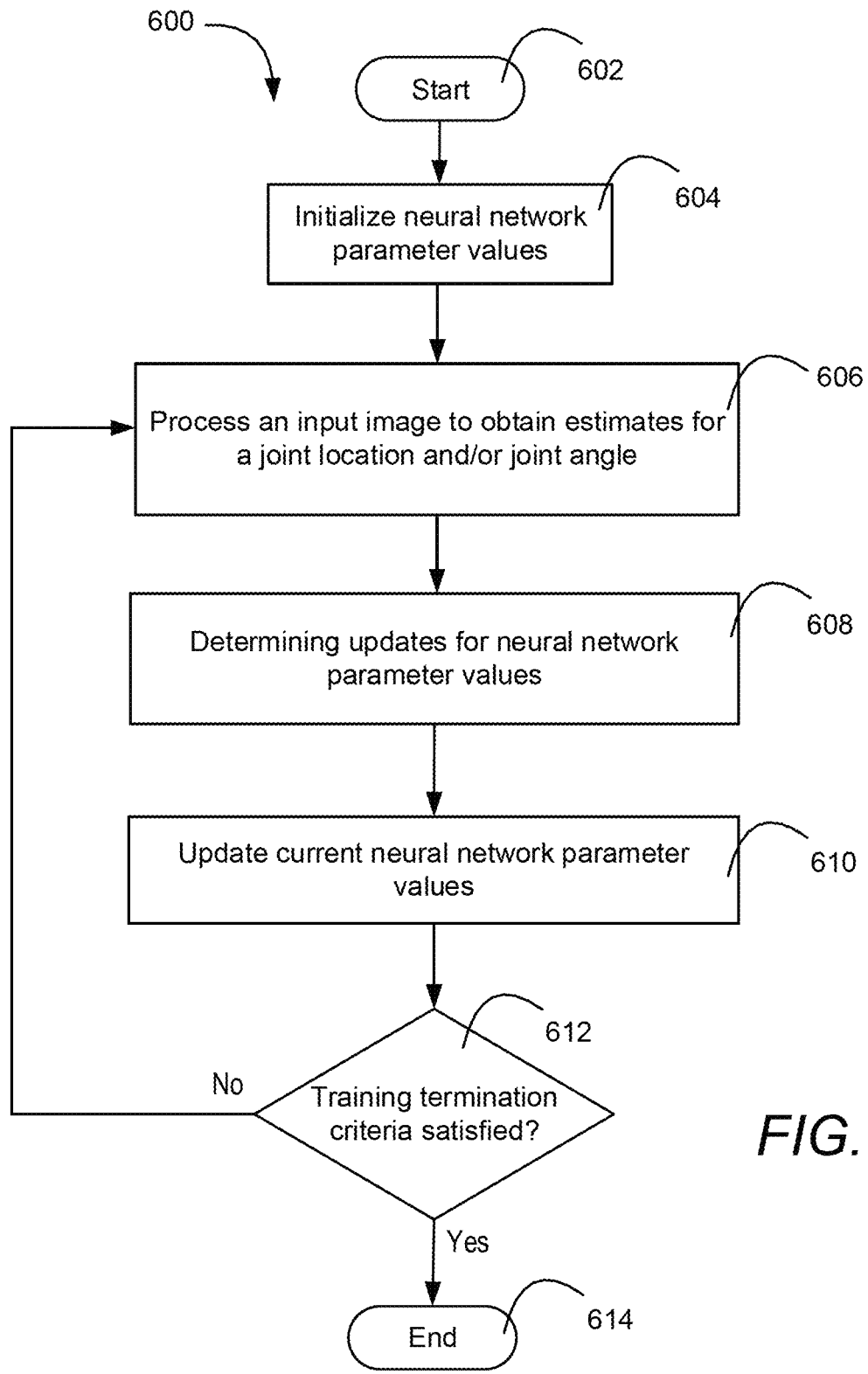
FIG. 6 is a flow diagram of an example neural network training process.

FIG. 6 is a flow diagram of an example process 600 that may be implemented and executed during training of the neural network as described herein. The process 600 may be performed by a system of one or more computers (e.g., one or more processors) located in one or more locations. The process may start at 602 and, at 604, the system may initialize the neural network parameter values (e.g., weights associated with one or more layers of the neural network). For example, the system may initialize the neural network parameter values by sampling them from one or more probability distributions or based on parameter values of another neural network with similar architecture. At 606, the system may process a training image and/or other training data (e.g., such as information regarding joint locations/joint angles of a kinematic chain as described herein) using current parameter values of the neural network to estimate the location and/or joint angle of a target joint. At 608, the system may determine updates to the current parameter values of the neural network, e.g., based on an objective or loss function and a gradient of the function. As described herein, the objective function may be designed to minimize the difference between an estimated joint location and/or joint angle and the ground truth for the joint location and/or join angle. The objective function may be implemented using, for example, mean squared error between the ground truth and the output of the neural network, based on L1 norm, etc. At 610, the system may update the current values of the neural network parameters, for example, using a backpropagation procedure. At 612, the system may determine whether one or more training termination criteria are satisfied. For example, the system may determine that the training termination criteria are satisfied if the system has completed a pre-determined number of training iterations, or if the change in the value of the loss function between training iterations falls below a predetermined threshold. If the determination at 612 is that the training termination criteria are not satisfied, the system may return to 606. If the determination at 612 is that the training termination criteria are satisfied, the system may end the training process 600 at 614.

The hierarchical estimation techniques described herein may improve many aspects of human model recovery including, for example, the accuracy of pose and shape parameter estimation, the ability to infer a joint location and/or joint angle even when parts of the human body are blocked, etc. The training of the neural network as described herein may be conducted in ways that further enhance the networks' capability in these aspects. For instance, in example implementations, the training of the neural network may include intentionally skipping (e.g., in a random manner) one or more joint locations and/or joint angles in the training datasets while still making the neural network to attempt to achieve the same objective. Using the limb kinematic chain 300b in FIG. 3B as an example, to train the neural network to predict the location and/or joint angle of the end effector 308b when the end effector is blocked or missing from the view, the end effector 308b may be skipped during the training process and the neural network may learn to adjust the filtering weights or parameters to achieve the same objective of correctly predicting the joint location and/or joint angle of the end effector 308b, e.g., based on the dependency between the joints in the chain (e.g., the end effector 308b may depend on the wrist 306b, the elbow 304b and/or the should 302b). The neural network may utilize the backward estimation techniques described herein to facilitate the learning. For example, after inferring the location and/or angle of the end effector 308b, the neural network may perform a backward estimation using the inferred end effector 308b. And if the end effector 308b was indeed predicted correctly in the forward direction, the backward estimation should result in the location and/or angle of the shoulder 302b being predicted correctly because the shoulder 302b depends on the end effector 308b (e.g., in addition to one or more other points in the chain). This way, by training the neural network to achieve consistent results at the end of a forward-backward loop, the neural network is taught to predict the location and/or angle of a joint even if it is blocked or missing from the view.

Figure 7:
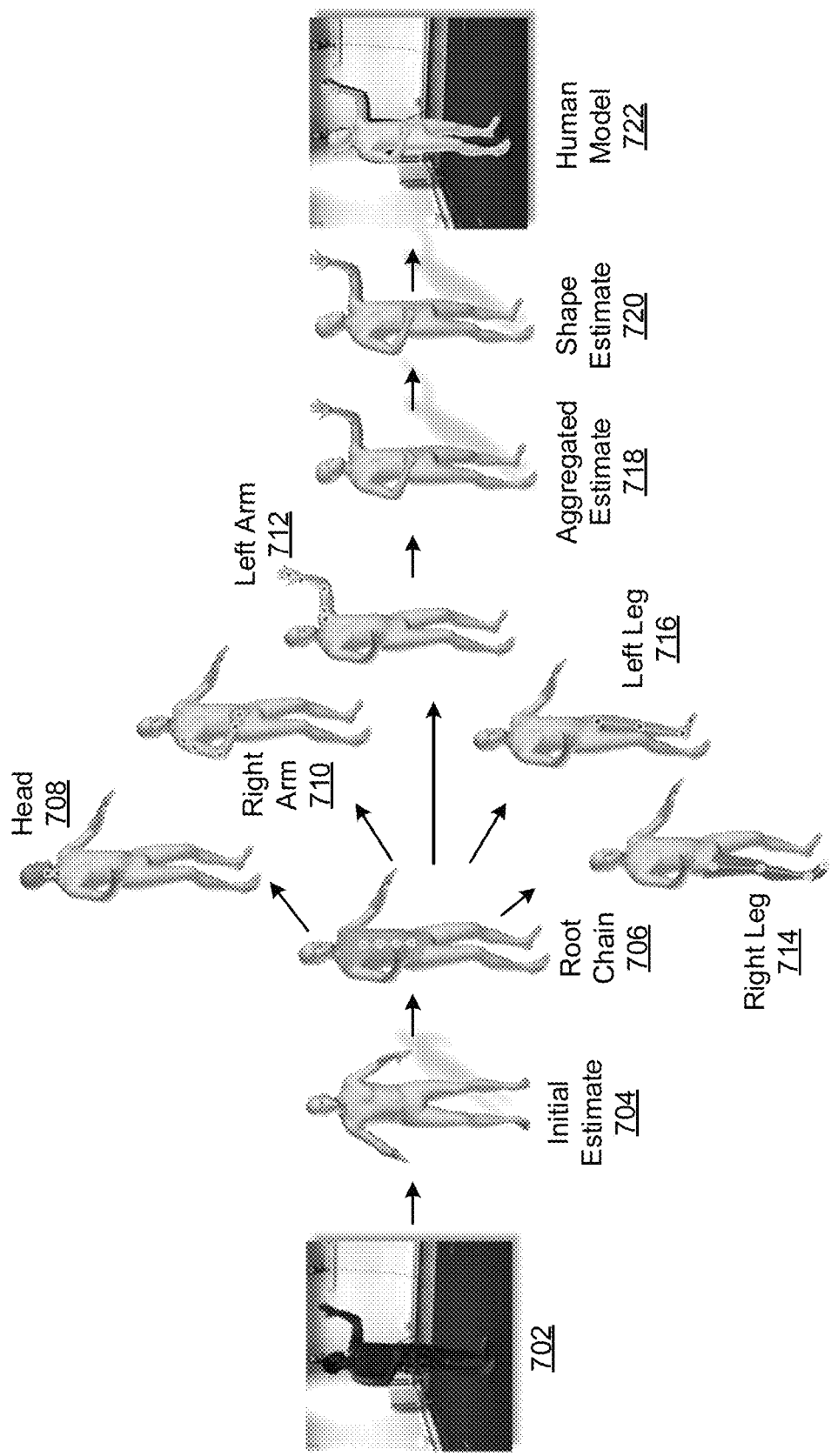
FIG. 7 is a diagram illustrating example operations that may be performed by an HMR system as described herein.

A system implementing the neural network described herein may utilize the structural correlation between different parts of the human body to estimate the parameters for recovering a human mesh model. FIG. 7 is a diagram illustrating example operations of such a system during human mesh model recovery. As described herein, the system may comprise one or more processors and one or more storage devices storing instructions that, when executed by the one or more processors, cause the one or more processors to carry out one or more of the following operations. The system may receive an input image 702 depicting one or more characteristics of a person. In response to receiving the input image 702, the system may analyze the image (e.g., at a pixel level) to extract a plurality of features Φ that is representative of the characteristics of the person (e.g., using an encoder module such as the encoder 204 in FIG. 2). Based on these extracted features, the system may determine initial parameter values 704 relating to the shape and/or pose of the person and further utilize the extracted features and the initial shape and/or pose parameter values 704 to estimate pose parameters 706 (e.g., joint locations and/or joint angles) associated with a root kinematic chain of the person. The estimates 706 for the root kinematic chain may then be used as a basis (e.g., together with the features Φ and/or the initial estimates of the shape parameters) for further predicting the pose parameters associated with one or more of a head kinematic chain 708, a right arm kinematic chain 710, a left arm kinematic chain 712, a right leg kinematic chain 714, or a left leg kinematic chain 716. In examples, the system may loop through each of the head or limb kinematic chains to estimate the respective pose parameters associated with the chain based on the pose parameters for the root kinematic chain, the features Φ extracted from the input image, and/or the initial shape parameters. In examples, the system may perform the pose parameter estimation for multiple (e.g., all) of the head or limb kinematic chains simultaneously (e.g., using respective processors or multiple computation threads) based on the pose parameters for the root kinematic chain, the features Φ extracted from the input image, and/or the initial shape parameters.

Once the pose parameters are derived for one or more of the kinematic chains shown in FIG. 7, the pose parameters may be aggregated to form an aggregated estimate 718 of the pose of the person. The system may then refine the estimate for the person's shape to obtain shape estimate 720 based on the features Φ extracted from the input image and the aggregated pose estimate 718, before the system recovers the human model 722 in accordance with the features Φ, the shape parameters 720, and/or the aggregated pose parameters 718, as described herein.

For simplicity of explanation, the operations of the system are depicted and described herein with a specific order. It should be appreciated, however, that these operations may occur in various orders, concurrently, and/or with other operations not presented or described herein. Furthermore, it should be noted that not all operations that the system is capable of performing are depicted in FIG. 7 and described herein. It should also be noted that not all illustrated operations may be required to be performed by the system.

Further, estimation of the pose parameters for the head or limb kinematic chains may be performed in any suitable order and is not limited to any one specific order. Or the estimation for all of the head and limb kinematic chains may be performed simultaneously based on the root kinematic chain. Additionally, the various functions described herein may be performed by one set of one or more neural networks or by respective sets of one or more neutral networks. For example, one set of one or more neural networks may be implemented and trained to estimate pose parameters for all of the head and limb kinematic chains or a respective set of one or more neural networks may be implemented and trained to estimate pose parameters for a respective head or limb kinematic chain.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus, comprising:
one or more processors configured to:
obtain an image of a person;
determine, based on one or more machine-learned (ML) models, respective angles of a first plurality of joints of the person based on the image of the person, wherein the first plurality of joints is associated with a root kinematic chain that includes a chest area or a pelvis area of the person, wherein the respective angles of the first plurality of joints include positional information about the first plurality of joints, and wherein the respective angles of the first plurality of joints and the positional information about the first plurality of joints indicate a position of the person as depicted in the image;
determine, based on the one or more ML models, respective angles of a second plurality of joints of the person based on the image of the person and the position of the person, wherein the second plurality of joints is associated with a head kinematic chain that includes a head area of the person or with a limb kinematic chain that includes a limb area of the person, and wherein the respective angles of the second plurality of joints are determined based on a range of joint angle values dictated by the position of the person; and
estimate a human model associated with the person based at least on the respective angles of the first plurality of joints of the person and the respective angles of the second plurality of joints of the person.

2. The apparatus of claim 1, wherein the one or more processors are further configured to determine a plurality of shape parameters associated with the person based on the image of the person, the respective angles of the first plurality of joints of the person, or the respective angles of the second plurality of joints of the person, and wherein the one or more processors are configured to estimate the human model based further on the plurality of shape parameters.

3. The apparatus of claim 1, wherein the one or more processors are further configured to output a representation of the human model to a receiving device associated with a medical imaging modality.

4. The apparatus of claim 1, wherein the root kinematic chain comprises a pelvis, a chest, and a spine of the person, wherein the limb kinematic chain comprises a first chain that includes a left shoulder, a left elbow, a left wrist, and a left hand of the person, a second chain that includes a right shoulder, a right elbow, a right wrist, and a right hand of the person, a third chain that includes a left hip, a left knee, a left ankle, and a left foot of the person, or a fourth chain that includes a right hip, a right knee, a right ankle, and a right foot of the person, and wherein the head kinematic chain comprises or a fifth chain that includes a head and a neck of the person.

5. The apparatus of claim 1, wherein the one or more ML models are trained using a plurality of training images and the training comprises inferring an end effector associated with the head kinematic chain or the limb kinematic chain based on one or more joint angles associated with the head kinematic chain or the limb kinematic chain.

6. The apparatus of claim 5, wherein the training of the one or more ML models comprises inferring, in a forward direction, the end effector associated with the head kinematic chain or the limb kinematic chain based on the one or more joint angles associated with the head kinematic chain or the limb kinematic chain, and inferring, in a backward direction, a joint angle associated with the head kinematic chain or the limb kinematic chain based on at least the end effector.

7. The apparatus of claim 5, wherein inferring the end effector based on the one or more joint angles associated with the head kinematic chain or the limb kinematic chain comprises skipping a joint angle of the one or more joint angles and inferring the end effector without the skipped joint angle.

8. The apparatus of claim 5, wherein the training of the one or more ML models comprises adjusting parameters of the one or more ML models based on an objective function that indicates a difference between an output of the one or more ML models and a ground truth associated with the output.

9. The apparatus of claim 8, wherein the objective function comprises a mean squared error (MSE) function.

10. The apparatus of claim 1, wherein at least one body area of the person is occluded in the image of the person.

11. A method, comprising:
obtaining an image of a person;
determining, based on one or more machine-learned (ML) models, respective angles of a first plurality of joints of the person based on the image of the person, wherein the first plurality of joints is associated with a root kinematic chain that includes a chest area or a pelvis area of the person, wherein the respective angles of the first plurality of joints include positional information about the first plurality of joints, and wherein the respective angles of the first plurality of joints and the positional information about the first plurality of joints indicate a position of the person as depicted in the image;

determining, based on the one or more ML models, respective angles of a second plurality of joints of the person based on the image of the person and the position of the person, wherein the second plurality of joints is associated with a head kinematic chain that includes a head area of the person or with a limb kinematic chain that includes a limb area of the person, and wherein the respective angles of the second plurality of joints are determined based on a range of joint angle values dictated by the position of the person; and estimating a human model associated with the person based at least on the respective angles of the first plurality of joints of the person and the respective angles of the second plurality of joints of the person.

12. The method of claim 11, further comprising determining a plurality of shape parameters associated with the person based on the image of the person, the respective angles of the first plurality of joints of the person, or the respective angles of the second plurality of joints of the person, wherein the human model associated with the person is estimated based further on the plurality of shape parameters.

13. The method of claim 11, wherein the root kinematic chain comprises a pelvis, a chest, and a spine of the person, wherein the limb kinematic chain comprises a first chain that includes a left shoulder, a left elbow, a left wrist, and a left hand of the person, a second chain that includes a right shoulder, a right elbow, a right wrist, and a right hand of the person, a third chain that includes a left hip, a left knee, a left ankle, and a left foot of the person, or a fourth chain that includes a right hip, a right knee, a right ankle, and a right foot of the person, and wherein the head kinematic chain comprises a fifth chain that includes a head and a neck of the person.

14. The method of claim 11, wherein the one or more ML models are trained using a plurality of training images and the training comprises inferring an end effector of the head kinematic chain or the limb kinematic chain based on one or more joint angles associated with the head kinematic chain or the limb kinematic chain.

15. The method of claim 14, wherein the training of the one or more ML models comprises inferring, in a forward direction, the end effector of the head kinematic chain or the limb kinematic chain based on the one or more joint angles associated with the head kinematic chain or the limb kinematic chain, and inferring, in a backward direction, a joint angle associated with the head kinematic chain or the limb kinematic chain based on at least the end effector.

16. The method of claim 14, wherein inferring the end effector based on the one or more joint angles associated with the head kinematic chain or the limb kinematic chain comprises skipping a joint angle of the one or more joint angles and inferring the end effector without the skipped joint angle.

17. The method of claim 11, wherein at least one body area of the person is occluded in the image of the person.

18. A method of training a machine-learned (ML) model, the method comprising:

obtaining a training image that depicts a human body;

determining, using present parameters of the ML model, respective angles of a first plurality of joints associated with the human body based on the training image, wherein the first plurality of joints is associated with a root kinematic chain of the human body, the root kinematic chain including a chest area or a pelvis area of the human body, wherein the respective angles of the first plurality of joints include positional information about the first plurality of joints, and wherein the respective angles of the first plurality of joints and the positional information about the first plurality of joints indicate a position of the human body as depicted in the training image;

determining, using the present parameters of the ML model, respective angles of a second plurality of joints associated with the human body based on the training image and the position of the human body, wherein the second plurality of joints is associated with a head kinematic chain of the human body that includes a head area of the human body or with a limb kinematic chain of the human body that includes a limb area of the human body, wherein the respective angles of the second plurality of joints are determined based on a range of joint angle values dictated by the position of the human body, and wherein determining the respective angles of the second plurality of joints comprises skipping a joint angle associated with the head kinematic chain or the limb kinematic chain and inferring an end effector associated with the head kinematic chain or the limb kinematic chain without the skipped joint angle, determining a difference between the determined angles of the second plurality of joints and a ground truth; and adjusting the present parameters of the ML model based on the difference between the determined angles of the second plurality of joints and the ground truth.

* * * * *